United States Patent [19]

Karami

[11] Patent Number: 4,585,449
[45] Date of Patent: Apr. 29, 1986

[54] DISPOSABLE DIAPER WITH IMPROVED TOP SHEET

[75] Inventor: Hamzeh Karami, Weston, Mass.

[73] Assignee: Colgate-Palmolive Co., New York, N.Y.

[21] Appl. No.: 725,459

[22] Filed: Apr. 22, 1985

Related U.S. Application Data

[63] Continuation of Ser. No. 458,510, Jan. 17, 1983, abandoned, and Ser. No. 292,475, Aug. 13, 1981, abandoned, which is a continuation of Ser. No. 13,711, Feb. 5, 1980, abandoned, which is a continuation of Ser. No. 913,714, Jun. 8, 1978, abandoned.

[51] Int. Cl.$^4$ .............................................. A41B 13/02
[52] U.S. Cl. ................................... 604/378; 604/382; 604/370
[58] Field of Search ............... 604/370, 381, 382, 365, 604/366, 372

[56] References Cited

U.S. PATENT DOCUMENTS 4,056,103 11/1977 Kaczmarzyk et al. ............. 604/370
4,077,410 3/1978 Butterworth et al. .............. 604/370

Primary Examiner—C. Fred Rosenbaum
Assistant Examiner—Sherri E. Vinyard
Attorney, Agent, or Firm—Herbert S. Sylvester; Murray M. Grill; Norman Blumenkopf

[57] ABSTRACT

A disposable product, such as a diaper, sanitary napkin or underpad, provided with a water impervious lower layer, an absorbent pad and a top sheet. The top sheet contains 0.1 to 0.6% by weight of a surfactant. The surfactant may be applied by spraying, printing, roller coating, etc., on the entire surface or, preferably, in limited areas such as in the central areas of the top sheet, or pay be line or spot printed thereon to improve fluid penetration, while retaining optimum fluid wetback and fluid retention characteristics. The top sheet is a hydrophobic sheet of excellent fluid penetration but resists fluid wetback.

2 Claims, 6 Drawing Figures

U.S. Patent  Apr. 29, 1986  4,585,449
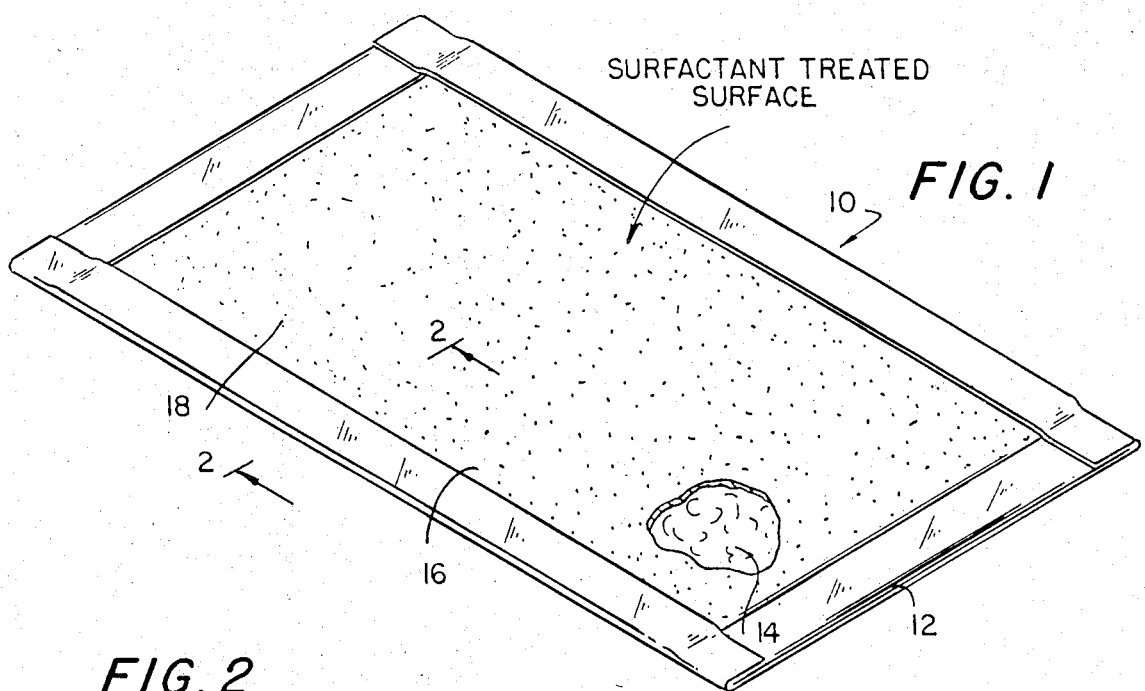
FIG. 1
FIG. 2
FIG. 3
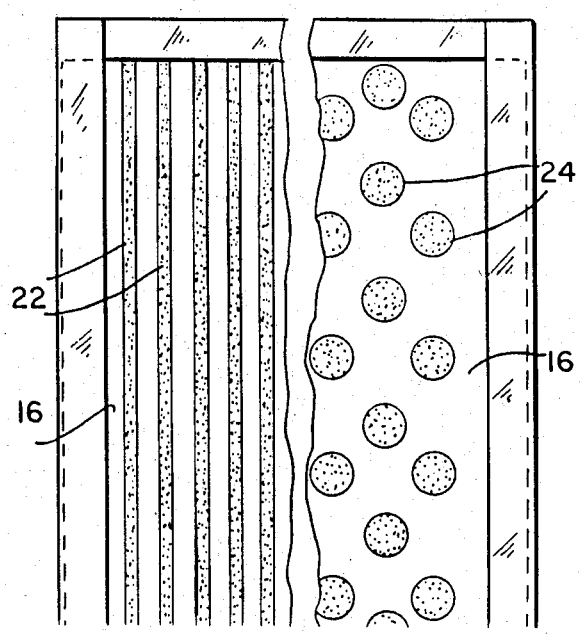
FIG. 4A  FIG. 4B
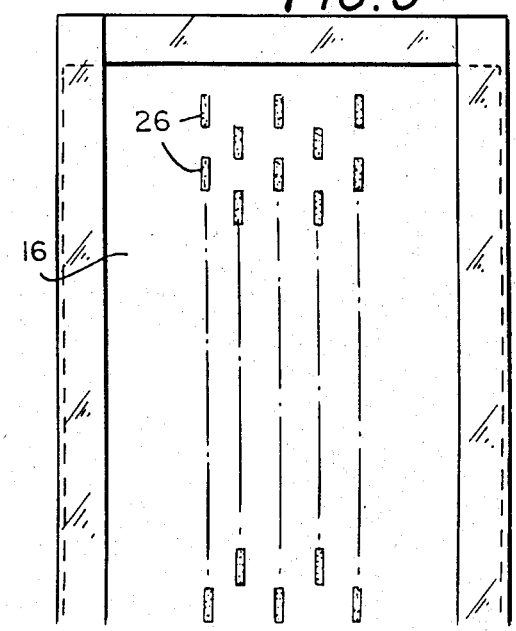
FIG. 5

DISPOSABLE DIAPER WITH IMPROVED TOP SHEET

REFERENCE TO RELATED APPLICATIONS

This application is a continuation of application Ser. No. 458,510, filed Jan. 17, 1983, application Ser. No. 292,475, filed Aug. 13, 1981, being the prior continuation, which in turn was a continuation of Ser. No. 13,711, filed Feb. 5, 1980, and which in turn was a continuation of application Ser. No. 913,714, filed June 8, 1978 now all abandoned.

BACKGROUND OF THE INVENTION

1. Field of the Invention

This invention relates to disposable products, such as diapers, sanitary napkins and underpads and, more particularly, to the top sheet construction thereof.

2. Description of the Prior Art

In the past, disposable products, particularly diapers, sanitary napkins and underpads, have been constructed with top sheets of hydrophobic material. This material has rather low fluid retention and fluid wetback characteristics and improvements in fluid penetration which are desirable especially to prevent leaking when there are rapid gushes of fluid material, such as urine, menstral fluid and the like. The hydrophobic sheets have in the past been made of non-woven polyamide, polypropylene, polyester fibers or mixtures of these and these hydrophobic top sheets have needed improvement in fluid penetration. To this end, U.S. Pat. No. 3,814,101 shows the use of a hydrophobic top sheet which is provided with a series of slits therein which slits serve as values. This hydrophobic top sheet is of a film-like material.

Hydrophobic non-woven materials have been used in diaper construction, such as shown in U.S. Pat. No. 3,987,786, which employs the use of a surfactant in particular areas on treated materials.

SUMMARY OF THE INVENTION

In accordance with the objects and purposes of the present invention, the disposable product construction includes an air permeable top sheet or hydrophobic non-woven material, based on polyamide, polypropylene or polyester material, which overlies the absorbent pad which in turn is underlined by a water-impervious film material. The top sheet is suitably treated with a surfactant, preferably non-ionic, to provide for more rapid fluid penetration while retaining optimum wetback and fluid retention characteristics. To this end, preferably only spaced areas of the top sheet are coated, such as by spraying the central area or line printing, spot printing in discrete areas of the top sheet.

BRIEF DESCRIPTION OF THE DRAWING

FIG. 1 is a perspective view of a diaper constructed in accordance with the concepts of the present invention with parts thereof broken away illustrating details of construction;

FIG. 2 is a vertical sectional detail view looking along the plane of line 2—2 in FIG. 1;

FIG. 3 is a schematic elevational view of a diaper;

FIG. 4a is a partial plan view illustrating a disposable diaper having line printed surfactant on the top sheet thereof;

FIG. 4b is a partial plan view of a diaper which has surfactant printed is discrete spaced areas thereon; and FIG. 5 is a plan view of a preferred embodiment of the invention wherein the central portion of the top sheet is line printed in spaced discrete areas with surfactant.

DETAILED DESCRIPTION OF THE INVENTION

With continuing reference to the accompanying drawing, wherein like reference numerals designate similar parts throughout the various views, reference numeral 10 generally designates a diaper which includes a bottom sheet 12 of water impervious plastic film material (which may be embossed or matte finished) having mounted thereon a pad 14 formed of an absorbent core, which may have one or more layers of wadding. The top sheet 16 is made of non-woven hydrophobic material, such as polypropylene, polyamide or polyester fibers. The top sheet is spunbonded, preferably of non-woven fibers of polyethylene, polypropylene or a combination thereof.

In accordance with the concepts of the present invention, the upper surface only of the top sheet is treated as at 18 with 0.1 to 0.6% by weight of a surfactant capable of altering the hydrophobic properties of the material on the top surface thereof. The surfactant is preferably a non-ionic and, more preferably, a ethoxylate of (1) an $C_{12}$ to $C_{20}$ alcohol (e.g. 5–20 moles of E.O.*), (2) a $C_6$ to $C_{10}$ alkyl phenol (e.g. 5–30 moles of E.O.*). A preferred non-ionic is "Triton X-100," (a 100 E.O.* condensate with octyl phenol), of the top sheet 16 and, as shown in FIG. 3, may be sprayed or surface printed as at 20 in only the central areas of the top sheet 16. Conventional roller coating may be used as well.

*E.O. is ethylene oxide

As shown in FIG. 4a, the surfactant may be line printed as at 22. Alternatively, the surfactant may be spot printed as at 24 in FIG. 4b in discrete areas at spaced intervals.

In a preferred embodiment, as shown in FIG. 5, the surfactant is line printed at 26 in spaced intervals on each line with the areas being printed in each line being staggered. Only the central portion of the top sheet is shown provided with the printed coating or surfactant. If desired, the entire surface may be so treated.

A particularly preferred line treatment is one wherein the lines 22, instead of being parallel to the sides of the diaper, are arranged diagonally (e.g. at an angle of from 30° to 60° with diaper edge). In a further desirable embodiment, the lines shown in FIG. 4a are rotated 90°.

In operation, fluid penetration is enhanced by the surfactant treated areas of the non-woven hydrophobic material to permit more rapid fluid penetration. However, little change of the desirable fluid wetback and fluid retention characteristics are evident. In the preferred top-surface treatment, the surfactant does not penetrate through the material, but only serves to initially guide the fluid material to penetrate the non-woven hydrophobic material, and this further limits wetback.

The treated top sheets of the present invention have a penetration factor of at least 80 and a wetback factore no greater than 10. These factors represent the percent of fluid which passes through the sheet in the test period time and the percent which "wets back" in the prescribed test. In the test procedures, 30 c.c. of fluid are used. If all passes through the sheet with no "roll off,"

the penetration factor is 100. If half rolls off, the factor is 50. Similarly, if 15 c.c. of fluid are wet back in the described procedure, the factor is 50. Obviously, the higher the penetration factor and the lower the wetback factor, the more desirable is the product.

What is claimed is:

1. A hydrophobic top sheet for a disposable product, said top sheet being permeable and being of spunbonded hydrophobic fibers being free of any binder and being selected from the group consisting of polyamide, polypropylene and polyester fibers and mixtures thereof, and from 0.1 to 0.6% by weight of a surfactant printed on the top surface of said top sheet to facilitate fluid passage therethrough but minimize wetback, said top sheet having a maximum wetback facter of 10 and a penetraction factor of at least about 80, said surfactant not extending below said top surface, said surfactant being printed in spaced spots.

2. A top sheet for a disposable product according to claim 1, wherein said surfactant is printed on the central areas only of said top sheet.

* * * * *